United States Patent
Atzler et al.

Patent Number: 5,933,232
Date of Patent: Aug. 3, 1999

[54] FLUORIMETER

[75] Inventors: Josef Atzler, Hallein; Karl Puchegger, Salzburg, both of Austria

[73] Assignee: Tecan Austria GmbH, Groedig, Australia

[21] Appl. No.: 08/855,359

[22] Filed: May 13, 1997

[30] Foreign Application Priority Data

May 31, 1996 [AT] Austria ................................. 326/96

[51] Int. Cl.[6] ..................................................... G01J 3/30
[52] U.S. Cl. ...................................... 356/317; 250/458.1
[58] Field of Search .................................. 356/318, 417, 356/317; 200/458.1, 459.1, 461.1, 461.2, 328; 422/82.08

[56] References Cited

U.S. PATENT DOCUMENTS

| | | |
|---|---|---|
| 4,296,326 | 10/1981 | Haslop et al. . |
| 4,626,684 | 12/1986 | Landa . |
| 5,155,046 | 10/1992 | Hui et al. . |
| 5,307,154 | 4/1994 | Naemura et al. . |

FOREIGN PATENT DOCUMENTS

| | | |
|---|---|---|
| 70171/87 | 9/1987 | Australia . |
| 0 516 274 | 12/1992 | European Pat. Off. . |
| 26 42 170 | 4/1977 | Germany . |
| 41 15 401 | 11/1992 | Germany . |
| 42 28 366 | 3/1994 | Germany . |
| 1 568 366 | 5/1980 | United Kingdom . |
| 2 196 734 | 5/1988 | United Kingdom . |

*Primary Examiner*—K P Hantis
*Attorney, Agent, or Firm*—Wenderoth, Lind & Ponack, L.L.P.

[57] ABSTRACT

A fluorimeter has a flash lamp, a measurement station with a receiver for microtitration plates, at least one measurement head disposed at the receiver and an evaluation station having a detector. Emission signals given off by a sample are evaluated by the detector. Light guides extend from the flash lamp to the measurement head from the measurement head to the detector. At the measurement station one measurement head is arranged above a sample and one measurement head beneath the sample. A change-over switch is formed by a pivotal bar which connects the light guides selectively to the upper or the lower measurement heads. On the pivotal bar are connections for the light guides which lead to the upper and the lower measurement heads. Connection of a respective measurement head can be brought selectively into correlation with the light source and the detector.

14 Claims, 3 Drawing Sheets

FLUORIMETER

BACKGROUND OF THE INVENTION

The invention relates to a fluorimeter having a light source for the emission of preferably flash light, a measurement station having a receiving means for at least one sample container, in particular for receiving microtitration plates, at least one measurement head disposed at the receiving means, and an evaluation station having a detector, preferably a photomultiplier (PMT) for evaluation of emission signals (light) given off by the sample. Light guide means lead from the light source to the measurement head and from the measurement head to the detector.

Many molecules and molecular systems, upon light irradiation in particular with high-energy UV-radiation, exhibit a quite specific emission of light, which is referred to as photoluminescence. This predominantly involves fluorescence and phosphorescence. Such phenomenon is used to an increasing degree in relation to laboratory samples, for example blood samples in microtitration plates.

When using conventional fluorimeters the samples can be measured from above or from below. A change in the measurement direction is either not possible at all or requires expensive conversion of the measurement arrangement.

SUMMARY OF THE INVENTION

The object of the present invention is to provide an improved measurement arrangement of the above type in such a way that samples can be measured both from below and from above without necessitating conversion of the fluorimeter.

In accordance with the invention such object is attained in that at the measurement station at least one measurement head is arranged above the sample and one measurement head is arranged below the sample, and that there is provided a change-over switching means which can be connected by way of light guide means selectively to the upper or to the lower measurement head by means of connections on the measurement head.

It is advantageously provided that the change-over switching means is formed by a pivotal bar on which are provided connections for the light guide means which go to the upper and to the lower measurement heads, wherein the connections of a respective measurement head can be brought selectively into contact with the light source and with the detector.

In order to enable the user to check the plate definitions of microtitration plates and to determine the same in the case of different microtitration plates, an advantageous embodiment of the invention provides that the pivotal bar is provided with a connection for a light guide means of a transillumination measurement means (ELISA).

BRIEF DESCRIPTION OF THE DRAWINGS

An embodiment of the invention is described in greater detail hereinafter with reference to the accompanying drawings, wherein.

DETAILED DESCRIPTION OF THE INVENTION

Figure 1:
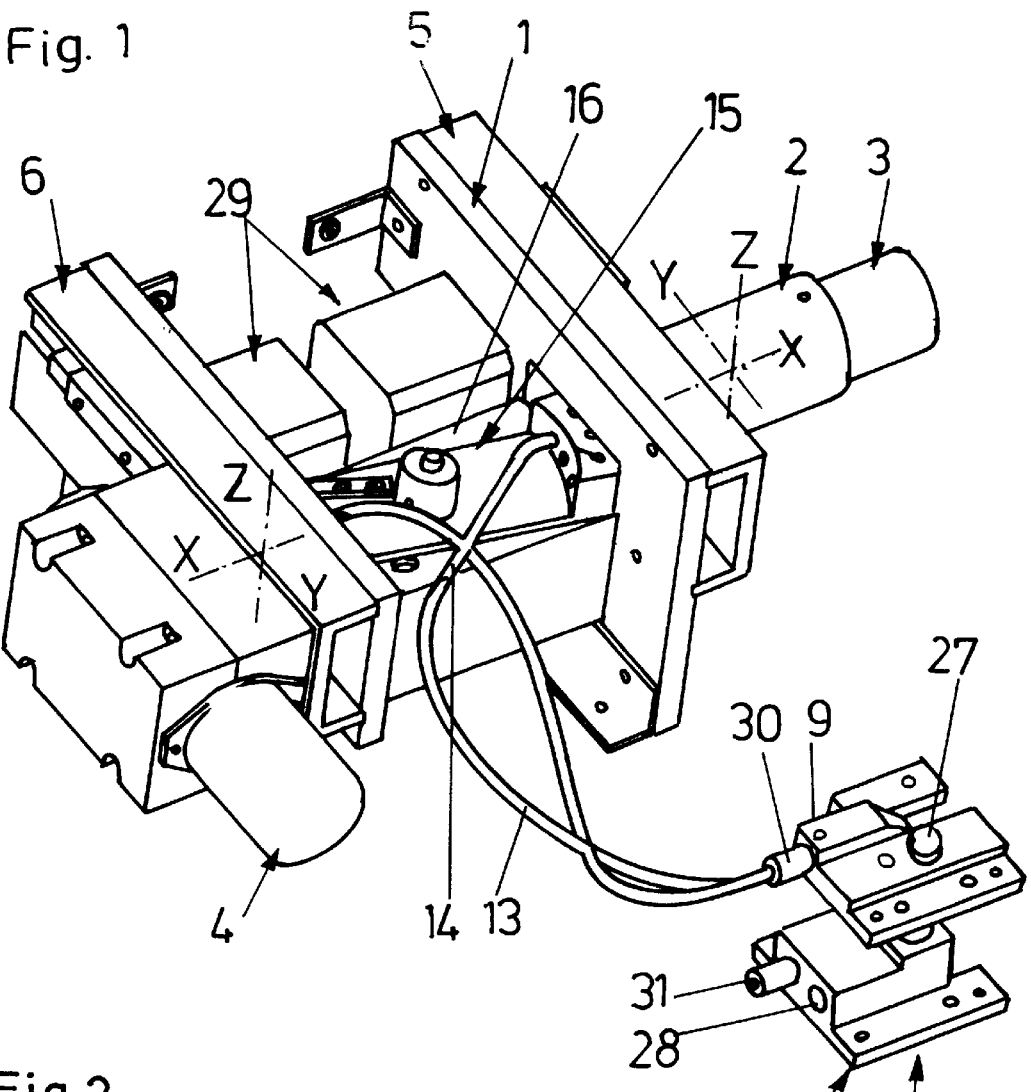
FIG. 1 is a perspective view of a fluorimeter according to the invention.

Feed and holding devices for microtitration plates 12 are not shown in the drawings. They are designed in accordance with the conventional state of the art. Likewise, FIG. 1 does not show light guide means for a lower measurement head 11, for the sake of enhanced clarity.

Figure 3:
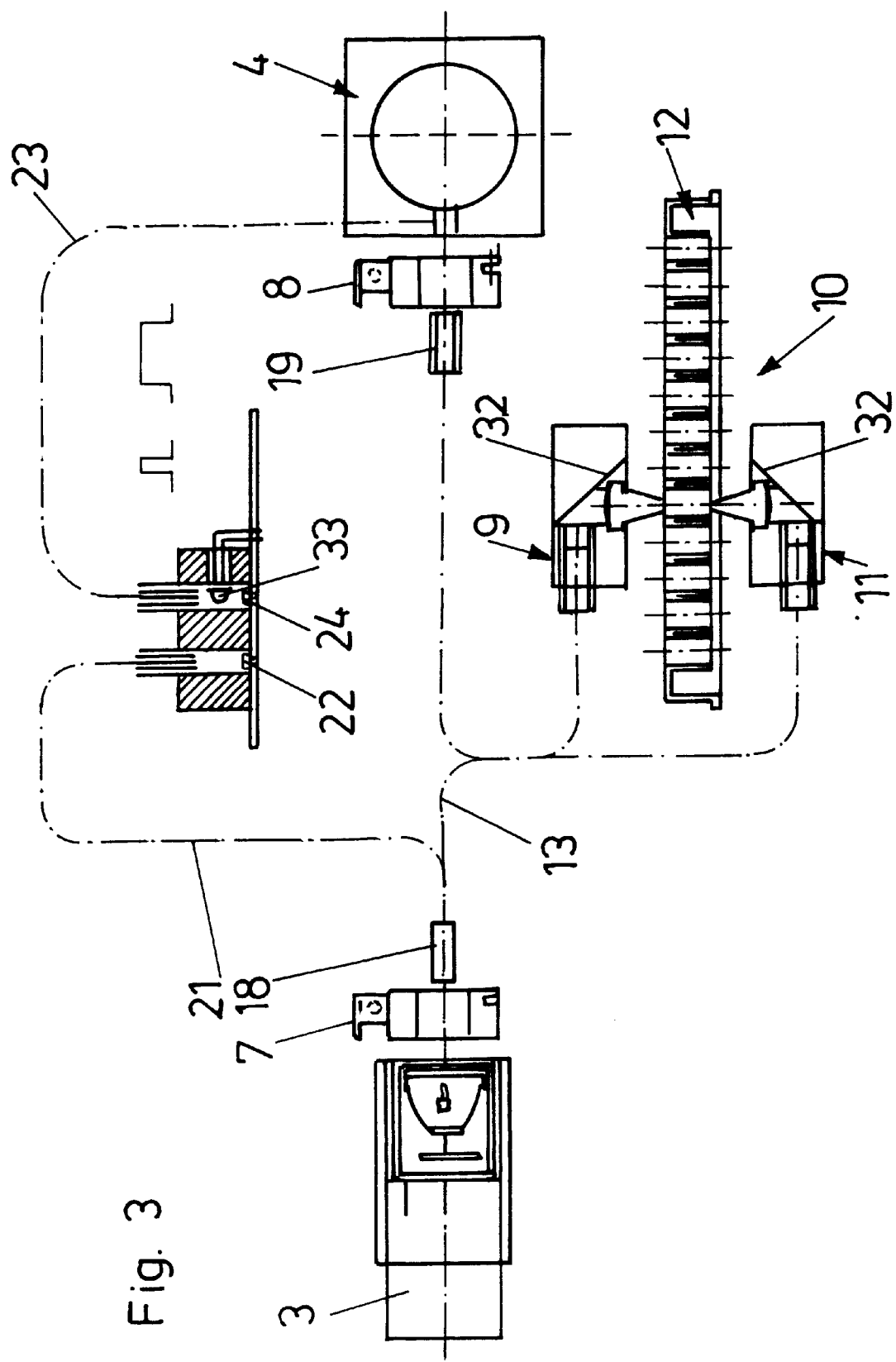
FIG. 3 is a diagrammatic view of the fluorimeter.
Figure 4:
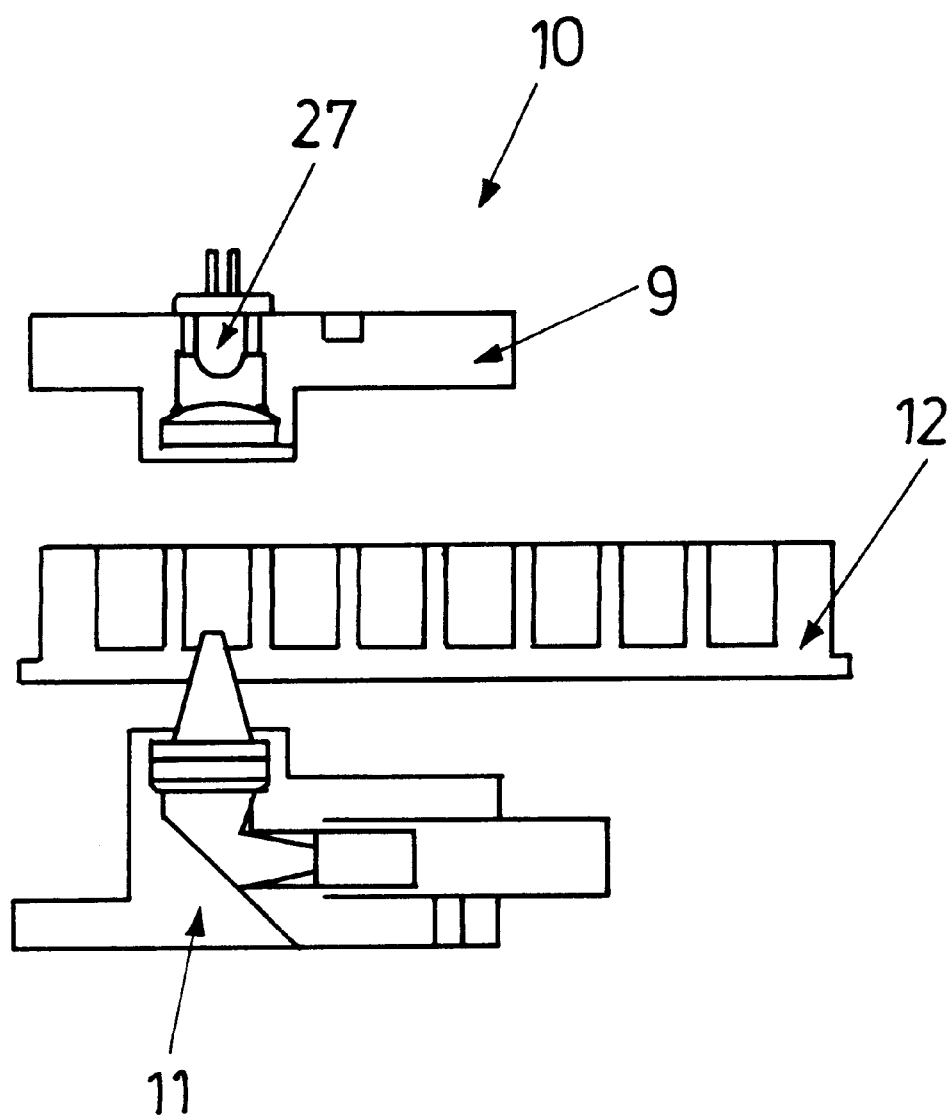
FIG. 4 is a diagrammatic view of measurement heads in a region of transillumination measurement.

The fluorimeter according to the invention has a frame and support portion 1 which at one side carries a holder 2 for a flash lamp 3 and at the other side a detector 4 formed by a photomultiplier. Provided downstream of the flash lamp 3 and upstream of the detector 4 are respective filter guides 5, 6 for an excitation filter 7 and an emission filter 8 (FIG. 3). The filters 7, 8 determine the band width and wavelength of light involved in the fluorescence measurement procedure. They are displaceable by way of motors 29 in the filter guides 5, 6 so that it is possible to operate with different wavelengths.

Arranged at a measurement station 10 is an upper measurement head 9 and lower measurement head 11. Microtitration plate 12 is movable between the two measurement heads 9, 11. It is however also possible for the microtitration plate 12 to be held immobile during the measurement operation while the measurement heads 9, 11 are moved above or below the microtitration plate 12. Measurement heads 9, 11 are provided with respective connections 30, 31 for light guide means including light guide portions 13, 14, wherein the light guide portion 13 runs to the flash lamp 3 and the light guide portion 14 runs to the detector 4.

Figure 2:
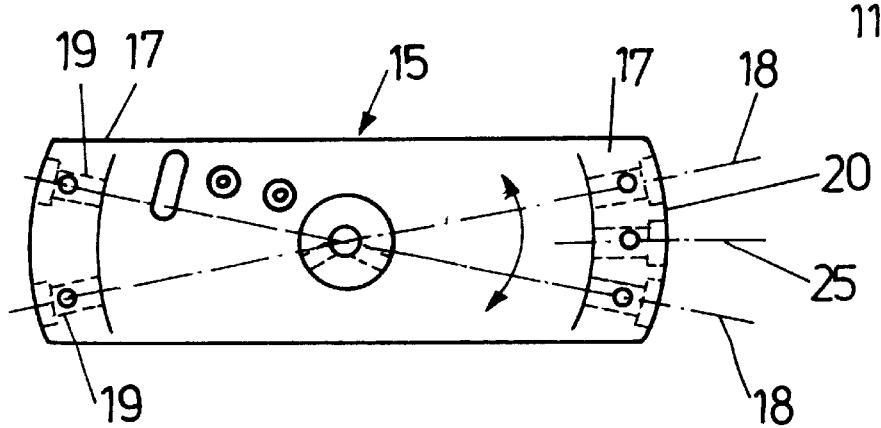
FIG. 2 is a plan view of a pivotal bar thereof.

The light guide means 13, 14 are formed by fiber bundles, for example of plastic, quartz or glass fibers, and are fixed to a pivotal bar 15. The pivotal bar 15 is pivotable about a perpendicular axis 16 in the direction of the double-headed arrow in FIG. 2. At its ends bar 15 has two supports or holders 17 in which are disposed connections 18, 19 for the light guide means 13, 14. Connections 18, 19 are disposed in mutually diagonally opposite relationship on the pivotal arm 15. Either the upper measurement head 9 or the lower measurement head 11 is connected to the flash lamp 3 or the detector 4 by way of respective connections 18, 19 of the pivotal arm 15. The end faces 20 of the supports 17 correspond to portions of a cylinder.

Arranged in each measurement head 9, 11 is a mirror 32 which is disposed at an angle of 45° relative to the direction of incidence of the light. By virtue of the mirrors 32, the structural height of the measurement heads 9, 11 can be kept extremely small.

Arranged between the flash lamp 3 and the light guide means 13 which lead to the measurement heads 9, 11 is excitation filter 7 which transmits light of a given wavelength. In addition, a light guide means 21 extends from the flash lamp 3 to a photoelectric diode 22 by means of which the flash energy is continuously monitored. Fluctuations in the flash energy can therefore be taken into consideration when calculating a fluorescence measurement result.

Inserted between the connection 19 of the light guide means 14 and the detector 4 is emission filter 8 which, like the emission filter 7, only transmits light of a given wavelength. From the detector 4 a light guide means 23 extends to a photoelectric diode 24 by means of which the detector 4 is monitored. As the detector 4 is not absolutely stable it may also vary in terms of its properties during measurement of the samples in a microtitration plate 12.

With the measurement arrangement according to the invention, an LED 33 is switched on for a short time between measurements of a microtitration plate 12, and both the monitoring photoelectric diode 24 and also the detector 4 are illuminated and read by an electronic system. In that way apparatus software can compare the values from the detector 4 to the very stable measurement values of the photoelectric diode 24 and take them into account in calculation of the RFU (relative fluorescence units) so that fluctuations in the characteristic of the detector 4 do not influence the measurement values.

Disposed on the pivotal bar 15 between the two connections 18 which are associated with the flash light 3 is a connection 25 for a light guide means which also leads to the lower measurement head 11 and by means of which ELISA measurement is possible. Beside the connection 31 for the light guide means 14 the lower measurement head 11 also has a further connection 28 for a light guide means which is connected to the connection 25 of the pivotal bar 15.

A photoelectric diode 27 is arranged in the upper measurement head 9. ELISA measurement is effected by way of the light guide means 28 and the photoelectric diode 27. Each microtitration plate can be scanned in the X- and Y-directions by a fine light beam emitted by the light guide means 28, and thus an image of the microtitration plate 12 can be produced. That image is represented on a PC-display screen by means of a software program and the measurement positions of a previously unknown microtitration plate 12 are defined by way of a graphic input by the user.

We claim:

1. A fluorimeter for measuring photoluminescence of a sample, said fluorimeter comprising:
   a measurement station including a receiver for receipt of a sample, an upper measurement head to be positioned above the sample in said receiver, and a lower measurement head to be positioned below the sample in said receiver;
   a light source for emission of light;
   an evaluation station including a detector for evaluation of emission signals emitted by the sample;
   first light guide means for passing light from said light source to said upper measurement head and from said upper measurement head to said detector;
   second light guide means for passing light from said light source to said lower measurement head and from said lower measurement head to said detector; and
   a change-over switch movable between a first position connecting said first light guide means to said light source and to said detector and a second position connecting said second light guide means to said light source and to said detector.

2. A fluorimeter as claimed in claim 1, wherein said receiver is operable to receive a microtitration plate containing the sample.

3. A fluorimeter as claimed in claim 1, wherein said detector comprises a photomultiplier.

4. A fluorimeter as claimed in claim 1, wherein said first light guide means is connected at respective connections at said upper measurement head and said change-over switch, and said second light guide means is connected at respective connections at said lower measurement head and said change-over switch.

5. A fluorimeter as claimed in claim 1, wherein each of said first and second light guide means comprises a first light guide portion extending from said change-over switch to the respective said upper or lower measurement head and a second light guide portion extending from said respective upper or lower measurement head to said change-over switch.

6. A fluorimeter as claimed in claim 1, wherein said change-over switch comprises a bar mounted for pivotable movement between said first and second positions.

7. A fluorimeter as claimed in claim 6, wherein said bar has first connections for said first light guide means to said light source and to said detector and second connections for said second light guide means to said light source and to said detector.

8. A fluorimeter as claimed in claim 7, wherein said first connections are located at diagonally opposite positions of said bar relative to an axis of pivotable movement thereof, and said second connections are located at different diagonally opposite positions of said bar relative to said axis thereof.

9. A fluorimeter as claimed in claim 7, wherein said connections are located at opposite ends of said bar.

10. A fluorimeter as claimed in claim 9, wherein said opposite ends are convex and have surfaces coaxial about an axis of pivotable movement of said bar.

11. A fluorimeter as claimed in claim 7, further comprising further connections on said bar and on one of said upper and lower measurement heads for attachment of a light guide for a transillumination measuring device for measuring transmission of light from said one measurement head through the sample in said receiver to the other said measurement head.

12. A fluorimeter as claimed in claim 11, further comprising a photoelectric diode on said other measurement head for receipt of the light transmitted through the sample.

13. A fluorimeter as claimed in claim 11, wherein said further connection on said bar is positioned between respective said first and second connections thereon to said light source.

14. A fluorimeter as claimed in claim 1, wherein said first and second light guide means comprise respective fiber bundles.

* * * * *

UNITED STATES PATENT AND TRADEMARK OFFICE
CERTIFICATE OF CORRECTION

PATENT NO. :   5,933,232
DATED      :   August 3, 1999
INVENTOR(S) :  Josef ATZLER et al.

It is certified that error appears in the above-identified patent and that said Letters Patent is hereby corrected as shown below:

On the title page, the Assignee information should read:
-- [73] Assignee:    Tecan Austria GmbH, Groedig, Austria--.

Signed and Sealed this

Twenty-first Day of March, 2000

Attest:

Attesting Officer

Q. TODD DICKINSON

Commissioner of Patents and Trademarks